United States Patent
Mousnier et al.

(10) Patent No.: US 7,479,497 B2
(45) Date of Patent: *Jan. 20, 2009

(54) USE OF QUINOLINE DERIVATIVES WITH ANTI-INTEGRASE EFFECT AND APPLICATIONS THEREOF

(75) Inventors: Aurélie Mousnier, Paris (FR); Catherine Dargemont, Paris (FR); Sabine Bonnenfant, Paris (FR); Hervé Leh, Paris (FR); Jean-François Mouscadet, Sceaux (FR); Fatima Zouhiri, Chatenay-Malabry (FR); Jean D'Angelo, Massy (FR); Didier Desmaele, Fresnes (FR)

(73) Assignees: Bioalliance Pharma SA, Paris (FR); Institut Gustave Roussy, Villejuif (FR); Centre National de la Recherche Scientifique (C.N.R.S.), Paris (FR); Inserm, Paris (FR); Universite de Paris 11- Paris Sud, Orsay (FR)

( * ) Notice: Subject to any disclaimer, the term of this patent is extended or adjusted under 35 U.S.C. 154(b) by 17 days.

This patent is subject to a terminal disclaimer.

(21) Appl. No.: 10/514,631

(22) PCT Filed: May 15, 2003

(86) PCT No.: PCT/FR03/01487

§ 371 (c)(1),
(2), (4) Date: Jul. 20, 2005

(87) PCT Pub. No.: WO03/096965

PCT Pub. Date: Nov. 27, 2003

(65) Prior Publication Data

US 2005/0261336 A1    Nov. 24, 2005

(30) Foreign Application Priority Data

May 17, 2002    (FR)    ................... 02 06126

(51) Int. Cl.
*A61K 31/47*    (2006.01)
(52) U.S. Cl. ................................. 514/311
(58) Field of Classification Search .............. 514/311
See application file for complete search history.

(56) References Cited

U.S. PATENT DOCUMENTS 6,670,377 B1 *  12/2003   Mekouar et al.  ............ 514/314

FOREIGN PATENT DOCUMENTS

FR           2 761 687 A       10/1998
WO      WO 03 031413 A        4/2003

OTHER PUBLICATIONS

Zouhiri et al. "Structure-activity relationship and binding mode of styryquinolines as potent inhibitor of HIV-1 integrase and replication of HIV-1 in cell culture," J. Med. Chem. 2000, vol. 43, pp. 1533-1540.*

(Continued)

*Primary Examiner*—Shengjun Wang
(74) *Attorney, Agent, or Firm*—Foley & Lardner LLP

(57) ABSTRACT

The invention relates to the use of 8-hydroxyquinoline 7-carboxylic acid derivatives in order to produce integrase-inhibiting medicaments, capable of blocking viral replication in the stages preceding integration, and if appropriate at the level of this integration stage, these medicaments being usable for the treatment of retroviral pathologies, in particular for the treatment of AIDS.

9 Claims, 4 Drawing Sheets

OTHER PUBLICATIONS

Khalid Mekouar et al., "Styrlquinoline Derivatives: A New Class of Protent HIV-1 Intergase Inhibitors that Block HIV-1 Replication in CEM Cells", J. Med. Chem. 1998, 41, pp. 2846-2857.

Mohammad Ouali et al., "Modeling of the Inhibition of Retroviral Intergrases by Styrylquinoline Derivatives", J. Med. Chem. 2000, 43, 1949-1957.

Mohammed Ouali et al., "Tautomers of styrylquinoline derivatives containing a methoxy substituent: Computation of their population in aqueous solution and their interaction with RSV integrase calalytic core", Acta Biochimica Polonica, vol. 47, No. 1, 2000, pp. 11-22.

J. d'Angelo et al., "HIV-1 integrase: the next target for AIDS therapy?", Pathol. Biol. 2001; 49, pp. 237-246.

Zouhiri F et al. "Structure-Activity Relationships and Binding Mode of Styrylquinolines as Potent Inhibitors of HIV-1 Integrase and Replication of HIV-1 in Cell Culture", Journal of Mecinal Chemistry, American Chemical Society, Washington, US, vol. 43, 2000, pp. 1533-1540.

Polanski et al., "Use of the Kohonen Neural Network for Rapid Screening of Ex Vivo Anti-HIV Activity of Styrlquinolines", J. Med. Chem., vol. 45, Oct. 10, 2002, pp. 4647-4654.

International Search Report.

* cited by examiner

USE OF QUINOLINE DERIVATIVES WITH ANTI-INTEGRASE EFFECT AND APPLICATIONS THEREOF

A subject of the invention is the use of quinoline derivatives with anti-integrase effect and its applications.

The inhibiting effect of quinoline derivatives at the level of the integration of viral DNA into a host cell has already been reported.

In particular, such derivatives are described in Application FR 97 04 289 of 8th Apr. 1997 and Application FR 01 13209 of 12 Oct. 2001.

Study of these derivatives has shown that they act as competitors of viral DNA for binding to integrase.

The work of the inventors has now made it possible to demonstrate effects of the latter on the stages preceding the integration of viral DNA, in particular on reverse transcription and nuclear translocation.

Figure 1:
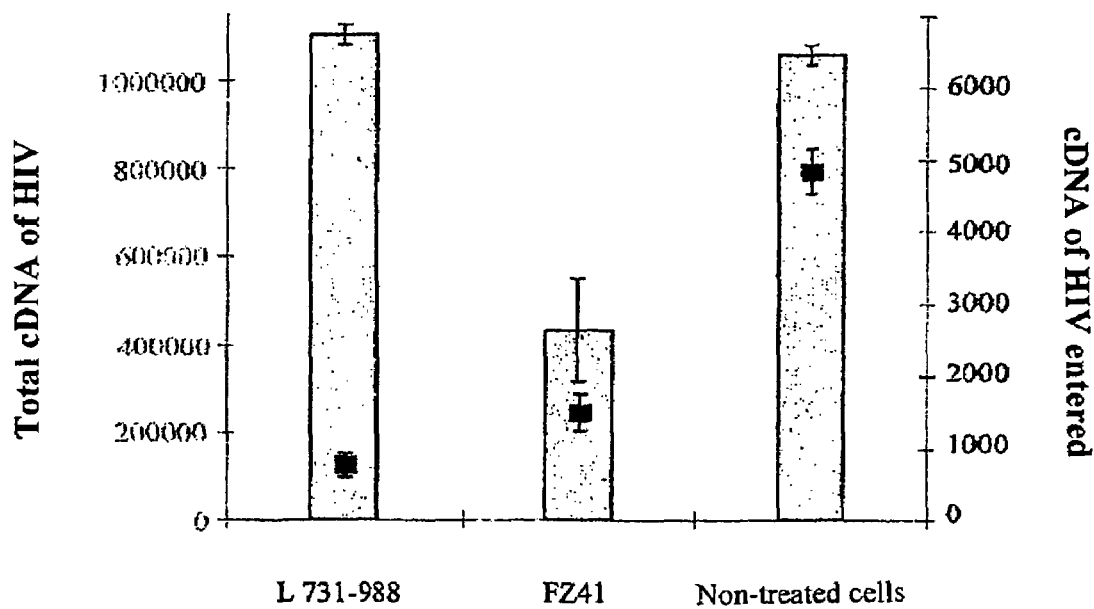
FIG. 1 is a graph showing the quantification of the total viral DNA synthesized 6 hours after infection and the quantity of viral DNA integrated into the genome 8 hours after infection.

The invention therefore has the purpose of providing a novel use of these quinoline derivatives in order to produce medicaments with an inhibiting effect on the activity of integrase, covering different stages after the entry of the virus into the cell, and in particular reverse transcription, nuclear translocation of viral DNA and integrase, and if appropriate the integration of viral DNA into the genome of the host cell.

The invention relates to the use of 8-hydroxyquinoline 7-carboxylic acid derivatives, or its pharmaceutically acceptable salts, in order to produce integrase-inhibiting medicaments, capable of blocking viral replication in the stages preceding integration, and if appropriate at the level of this integration stage, these medicaments being usable for the treatment of retroviral pathologies, in particular for the treatment of AIDS.

The derivatives used according to the invention are more particularly competitors of viral DNA for binding to integrase.

According to an embodiment of the invention, these are styrylquinolines, advantageously those defined in Application FR 97 04 289. It is recalled that, according to the most general definition given in this Application, these derivatives correspond to formula I

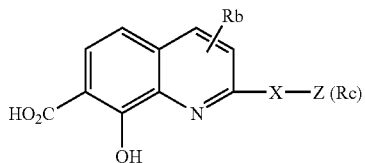

in which $R_b$ and $R_c$, identical to or different from one another, represent one or more substituents, themselves identical or different, occupying any position on the rings, this substituent or these substituents being chosen from a —$(CH_2)_n$—Y or —CH=CH—Y group, where Y represents a halogen atom, an —OH, —OR, —COH, —COR, —COOH, —COOR, —COH, —COR, —CONH$_2$, —CON ($R_x$, $R_y$) —CH=NOH, —CO—CH=NOH, —NH$_2$, —N($R_x$, $R_y$), —NO$_2$, —PO(OR)$_2$ —SH$_2$, —SR, —SO$_2$R, —SO$_2$NHR, CN, or Z($R_c$) radical, where R represents an alkyl radical with 1 to 8 carbon atoms, or an aryl or heterocyclic radical, $R_x$ and $R_y$, identical or different represent an alkyl radical with 1 to 5 carbon atoms, Z represents an aryl or heterocyclic radical and n is zero or an integer from 1 to 5, $R_b$ moreover being able to represent a hydrogen atom, and when Y represents a —COOH or —COOR group in $R_c$, Z, if it represents an aryl group, comprises at least 3 substituents or the quinoline nucleus is tri-substituted, X represents an ethylenic double bond, a —$(CH_2)_n$— group, where n is an integer from 1 to 5, or a —CH($R_d$)—CH($R_e$)— group, $R_d$ and $R_e$, identical or different, representing a hydrogen, halogen atom, a hydroxy or epoxy group, as well as the pharmaceutically acceptable salts of these derivatives, their diastereoisomeric forms and their enantiomeric forms.

The invention quite particularly relates to the use of 8-hydroxy-2-[2-[(3,4-dihydroxy,5-methoxyphenyl)ethenyl]]7-quinoline carboxylic acid, hereafter designated FZ41, of formula II

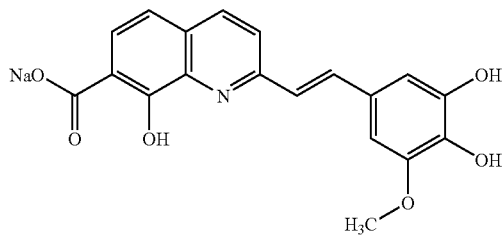

According to another embodiment of the invention, the derivatives used in order to produce said medicaments are 2-carbamoyl-8-hydroxyquinoline 7-carboxylic acid derivatives. In particular the invention relates to the use of the derivatives according to Patent Application FR 01 13 209. These derivatives, in their most general definition, are characterized in that they correspond to formula III

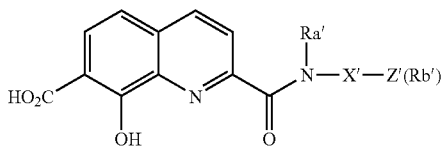

in which
- X' represents a —(CH$_2$)$_n$— alkyl chain in which n is equal to 0, 1 or 2, O, or N,
- Z' represents an aromatic ring which can comprise heteroatoms chosen from O, N or S, in substitution of the carbon atoms constituting said aromatic ring, this ring being able to be substituted or not substituted by Rb',
- Rb' represents 1 to 3 identical or different substituents, chosen from the —OH, —OR, —COOH, —COOR, —COH, —COR, —NH$_2$, —NH(R), —NH(R,R'), —SH and —SR and CN groups,
- Ra' represents a hydrogen atom or a —(CH$_2$)$_{n'}$—Y' group, for which n' is equal to 0, 1, 2 or 3 and Y' represents —CH$_3$, —COOH, —COOR, —CN, —OH, —OR, SR, or an aryl group optionally substituted by Rb',
- R and R', identical or different, represent a linear or branched alkyl chain with 1 to 4 carbon atoms, and their pharmaceutically acceptable salts.

Study of the properties of the derivatives used according to the invention has made it possible to demonstrate their effect on the stages prior to the integration of the viral DNA into the genome of the host cell with, if appropriate, an inhibiting effect at the level of the integration stage. These effects are directed against the reverse transcription of the retrovirus RNA of animal and human origin, and in particular of HIV-1, HIV-2, SIV, RSV and against the nuclear translocation of these retroviruses. The effectiveness of these derivatives is observed at submicromolar concentrations. IC$_{50}$s not exceeding 1 μM, advantageously 0.5 μM and even 0.1 μM are thus obtained.

These derivatives used according to the invention moreover have the advantage of considerable harmlessness and satisfactory bioavailability of the active drug.

These properties are therefore turned to good account according to the invention by using said derivatives as active ingredients of medicaments in combination with pharmaceutically acceptable vehicles. They can also be advantageously used in combination for multitherapies.

The dosages and administration methods are adapted depending on the treatment for each mono- or multitherapy used.

For multitherapies, said derivatives are advantageously presented in the same packaging in the form of kits.

Figure 2:
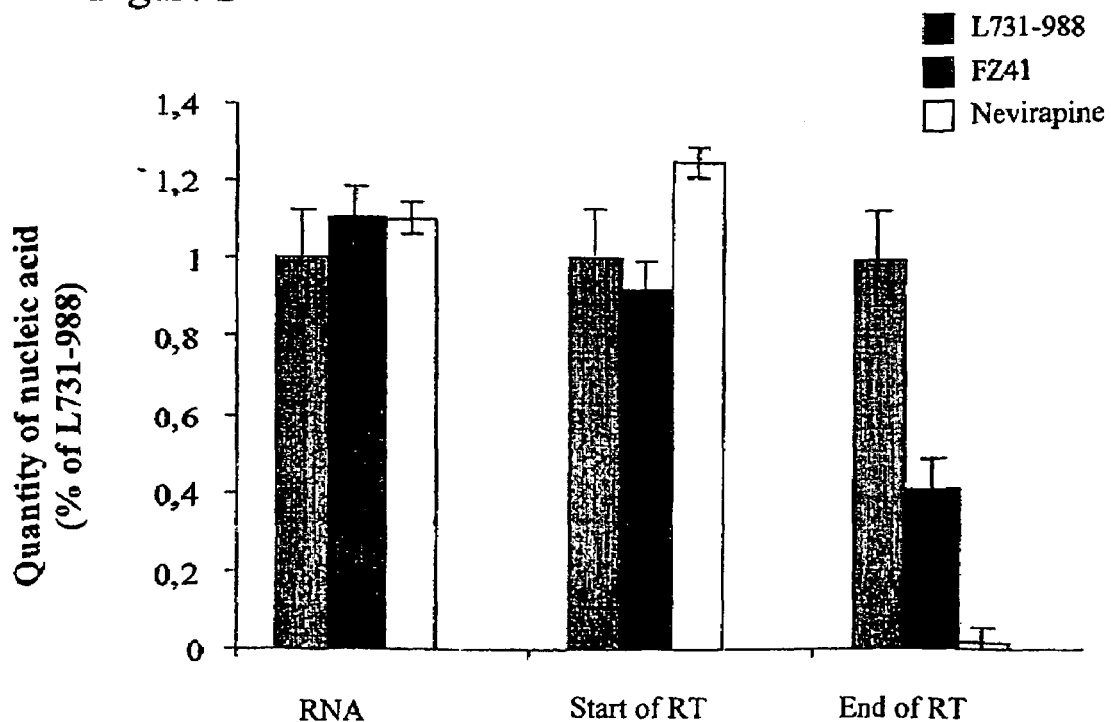
FIG. 2 is a graph of the quantity of RNA and genomic DNA having entered a cell after 1 hour and 30 minutes after infection, and the total DNA synthesized after 6 hours of infection.

Other characteristics and advantages of the invention are described in the examples which follow. In these examples, reference is made to FIGS. 1 and 2, which represent, respectively:

FIG. 1, the quantification of the total viral DNA synthesized 6 hours after infection and the quantity of viral DNA integrated into the genome 8 hours after infection, and FIG. 2, the quantity of RNA and that of genomic DNA having entered 1 hour 30 minutes after infection, and the total DNA synthesized 6 hours after infection.

Study of the Quantification of the Total Viral DNA Synthesized and of the DNA Integrated into the Genome of a Host Cell after Infection The operation described by Butler et al. in Nat. Med. 2001 May; 7 (5): 631-4 is carried out.

As shown in FIG. 1, it is noted with the molecule L731-988 (published by Hazuda et al. in Science, 28th Jan. 2000, 287 (5453): 646-50) that the DNA is perfectly synthesized, but only slightly or not at all integrated into the genome of the cell.

On the other hand, when administrating the FZ41, a strong reduction in the synthesis of viral DNA and in integration is noted.

Determination of the Quantity of RNA and Genomic DNA After Infection and of Total DNA Synthesized As control a non-nucleoside RT inhibitor, namely nevirapine (NNRTI) was used and, as products to be tested, L731-988 or FZ41.

The treatments carried out with these products do not lead to a reduction in the genomic RNA entering the cell 1 hour 30 minutes after infection. When comparing the data obtained at the start and at the end of the RT stage, the strong effect of the product used according to the invention and according to the control is noted.

Study of the Effect on the Viral Replication Cycle

Figure 3:
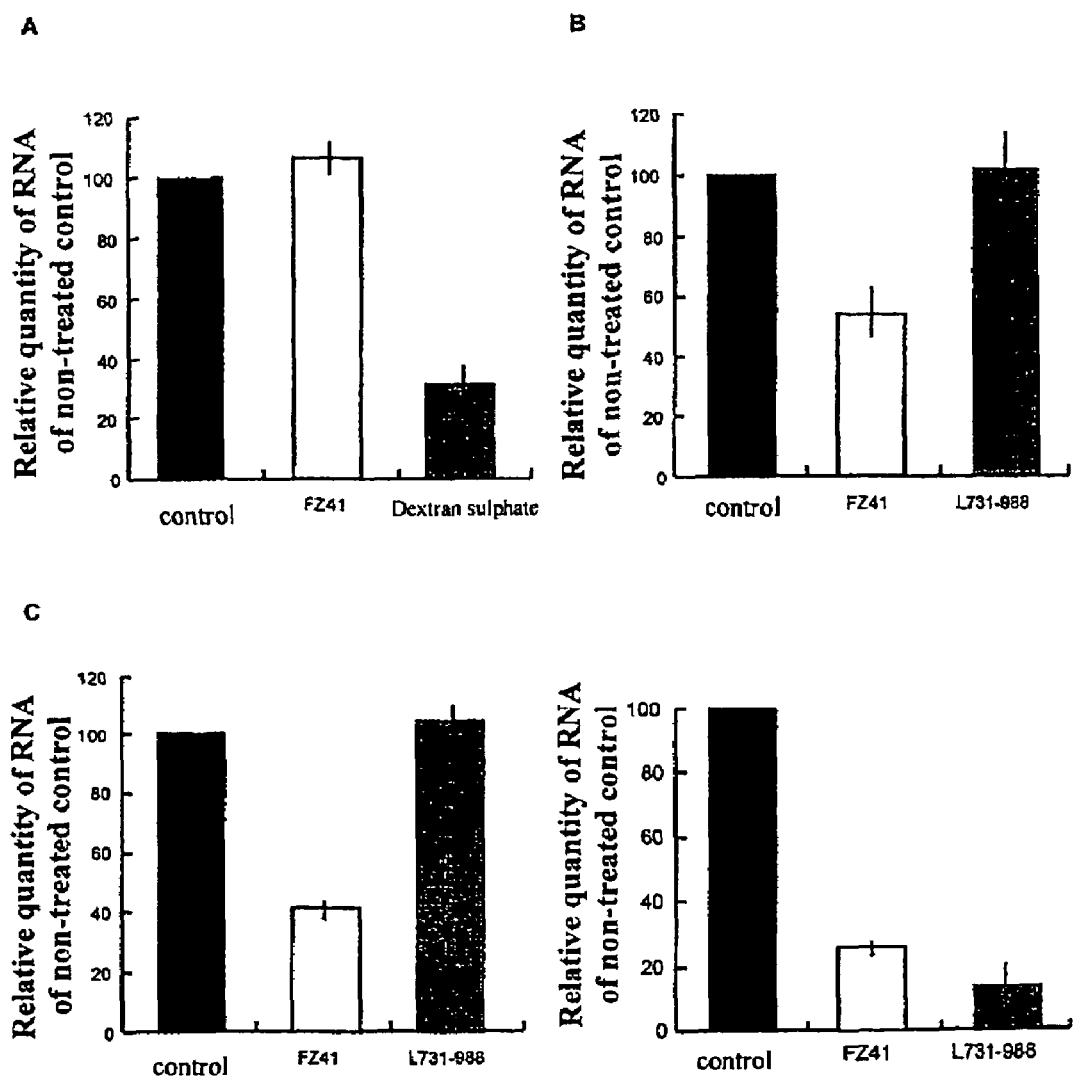
FIG. 3 is a graph of the quantification of the viral nucleic species by quantitative PCR in cells infected by HIV.

FIG. 3 shows the quantifications of the viral nucleic species by quantitative PCR in cells infected by HIV and treated or not treated with FZ41, a non-specific inhibitor of the entry of the virus (dextran sulphate) or an integration inhibitor (L731-988).

A: quantification by Q-PCR of the intracellular genomic RNA.

B: quantification by Q-PCR of the cDNA retrotranscribed at the start of retrotranscription C: quantification by Q-PCR of the cDNA retrotranscribed at the end of retrotranscription D: quantification by Q-PCR of the cDNA integrated into the host genome The results obtained show that styrylquinoline derivatives having an inhibiting activity on integrase and more particularly containing the pharmacophore described in patents FR 2 761 687 A and FR 01 13 209 inhibit the synthesis of retroviral DNA from the start of reverse transcription, but do not affect the quantity of viral genomic RNA penetrating into the cells.

Selection of Resistant Mutants

Culture of the virus in the presence of increasing concentrations of FZ41 allowed the emergence of viruses resistant to the drug. The mutations which appeared in these viruses are situated in the integrase at positions V165 and V249 on the one hand and at position C280 for a second virus. The mutants were generated by site specific mutagenesis and their resistance was verified.

Figure 4:
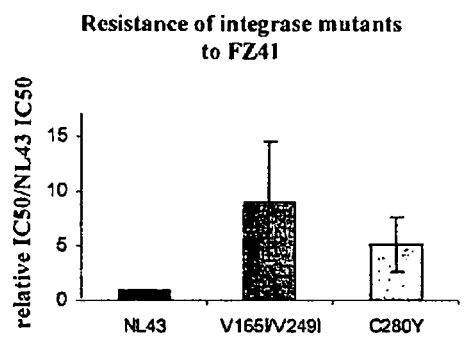
FIG. 4 is a graph of the resistance index obtained for each of the viruses.

FIG. 4 shows the resistance index obtained for each of the viruses, compare with the wild-type virus.

Effect of styrylguinolines on the Nuclear Translocation of the Integrase

Figure 5:
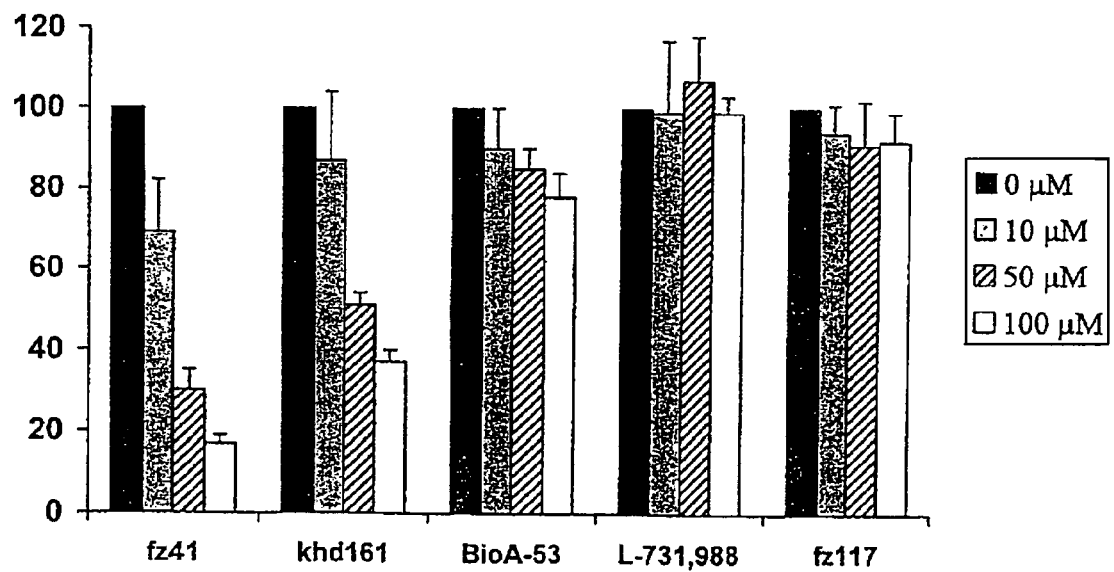
FIGS. 5 and 6 are graphs of the quantification of the fluorescence intensity measured in a nuclear import test on the integrase of HIV-1 in permeabilized HeLa cells in the presence or absence of cytoplasmic extracts.
Figure 6:
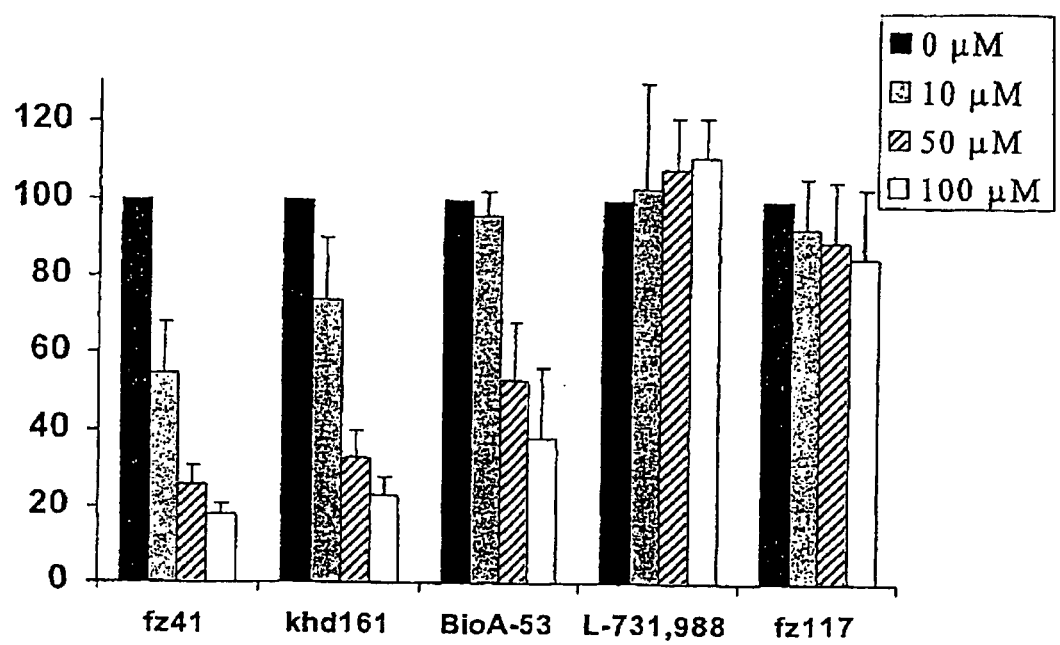

FIGS. 5 and 6 show the quantification of the fluorescence intensity measured in a nuclear import test on the integrase of HIV-1 in permeabilized HeLa cells in the presence or absence of cytoplasmic extracts.

The import tests in FIG. 5 were carried out as described in Depienne et al. 2001. HeLa cells were permeabilized with Digitonin, then incubated for 30 minutes at 30° C. with integrase coupled with Cyanine 3 fluorochrome in the presence of energy, in the absence of cytosolic extracts and in the presence or absence of increasing concentrations of different molecules as indicated. The cells were then fixed, analyzed by epifluorescence microscopy and acquisitions were carried out with a CCD camera.

For each condition, the fluorescence intensity per surface unit was quantified in 150 to 300 nuclei originating from 3 independent experiments.

Figure 7:
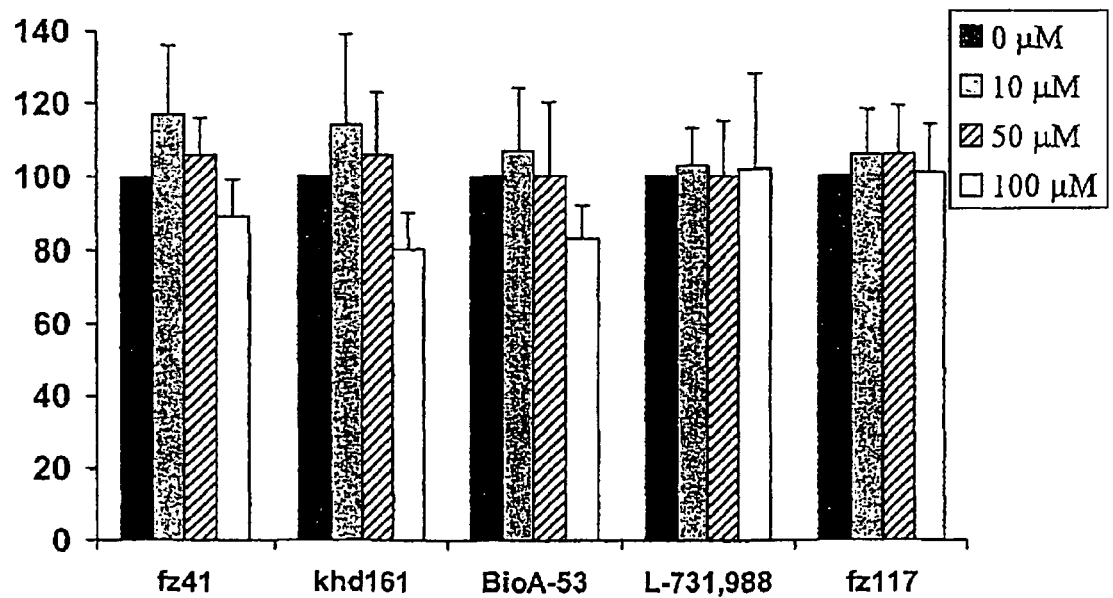
FIG. 7 is a graph of the quantification of the fluorescence intensity measured in a BSA-NLS nuclear import test in permeabilized HeLa cells.

FIG. 7 shows the quantification of the fluorescence intensity measured in a BSA-NLS nuclear import test in permeabilized HeLa cells The formulae of molecules used are given in the table below.

A contrario, the addition to the experiment of other integrase inhibitors (L731-988) or inactive styrylquinoline derivatives (FZ117) does not modify the nuclear import of the integrase.

The inhibition of this integrase translocation is specific since the nuclear import of BSA-NLS (Bovine serum albumin conjugated to a nuclear import signal) is not affected by the drugs (FIG. 6).

Moreover, the mutations obtained by selection with the FZ41 molecule and more particularly the V165I/V249I muta-

| Molecule | Formula | Integrase inhibitor in vitro |
|---|---|---|
| FZ41 | | YES |
| KHD161 | | YES |
| BioA53 | | YES |
| FZ117 | | NO |
| L731-988 | | YES |

The results obtained show that the styrylquinoline derivatives having an inhibiting activity on integrase and more particularly containing the pharmacophore described in patents FR 2 761 687 A and FR 01 13 209 inhibit the nuclear translocation of HIV integrase.

Thus, the FZ41 and KHD161 molecules considerably reduce the quantity of fluorescence obtained in the nuclei of permeabilized cells after treatment.

tions lead to a lack of the nuclear import of integrase in experiments on protein expression in eucaryotic cells.

The data of FIGS. 6 and 7 were obtained as follows: HeLa cells were permeabilized with digitonin, then incubated for 30 minutes at 30° C. with integrase conjugated to Cyanine 3 fluorochrome and with bovine serum albumin (BSA) conjugated to the standard nuclear localization signal of the T antigen of the SV40 virus (NLS) and with fluorescein (BSA-NLS), in the presence of cytosolic extracts and energy and in the presence or in the absence of increasing concentrations of different molecules as indicated. The cells were then fixed, analyzed by epifluorescence microscopy and acquisitions were carried out with a CCD camera. For each condition, the fluorescence intensity per surface unit was quantified in 150 to 300 nuclei originating from 3 independent experiments. FIG. 6 represents the results obtained with integrase and FIG. 7 those obtained with BSA-NLS.

BIBLIOGRAPHICAL REFERENCE

Depienne C, Mousnier A, Leh H, Le Rouzic E, Dormont D, Benichou S, Dargemont C. Characterization of the nuclear import pathway for HIV-1 integrase. J Biol Chem. May 25, 2001; 276(21): 18102-7.

The invention claimed is:

1. Method for inhibiting integrase and blocking viral replication in the stages preceding integration, and optionally at the level of this integration stage, for the treatment of retroviral pathologies, comprising administering to an animal or human in need thereof a 8-hydroxyquinoline 7-carboxylic acid derivative of formula III

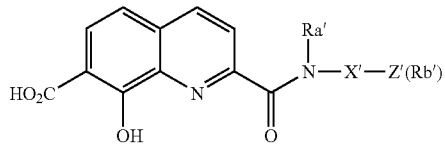

or a pharmaceutically acceptable salt thereof, wherein:
X' represents O, N, or an —(CH$_2$)$_n$— alkyl chain in which n is equal to 0, 1 or 2;
Z' represents an aromatic ring which can comprise heteroatoms selected from the group consisting of O, N and S in substitution of the carbon atoms constituting said aromatic ring, wherein Z' is substituted by 0-3 Rb' groups;
Rb', if present, at each occurrence is independently selected from the group consisting of —OR, —COOR, —COR, —NRR', —SR and CN; and
R and R', identical or different, are selected from the group consisting of H and a linear or branched alkyl chain with 1 to 4 carbon atoms.

2. Method according to claim 1, for the treatment of AIDS.

3. Method according to claim 1 or 2, wherein said derivatives are administered in multitherapies.

4. The method of claim 1, wherein the derivative of formula III is:

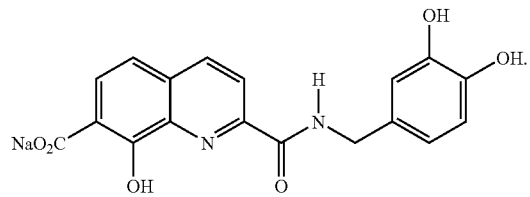

5. The method of claim 4, wherein th derivative is administered in multitherapies.

6. The method of claim 4, wherein the retroviral pathologies are selected from the group consisting of HIV-1, HIV-2, SIV, and RSV pathologies.

7. The method of claim 1, wherein the retroviral pathologies are selected from the group consisting of HIV-1, HIV-2, SIV, and RSV pathologies.

8. Method for inhibiting integrase nuclear import, comprising administering to an animal or human in need thereof a derivative of formula III

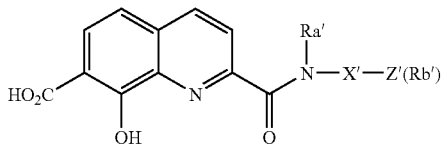

or a pharmaceutically acceptable salt thereof, wherein:
X' represents O, N, or an —(CH$_2$)$_n$— alkyl chain in which n is equal to 0, 1 or 2;
Z' represents an aromatic ring which can comprise heteroatoms selected from the group consisting of O, N and S in substitution of the carbon atoms constituting said aromatic ring, wherein Z' is substituted by 0-3 Rb' groups;
Rb', if present, at each occurrence is independently selected from the group consisting of —OR, —COOR, —COR, —NRR', —SR and CN; and
R and R', identical or different, are selected from the group consisting of H and a linear or branched alkyl chain with 1 to 4 carbon atoms.

9. A method for inhibiting integrase nuclear import, comprising administering to an animal or human in need thereof:

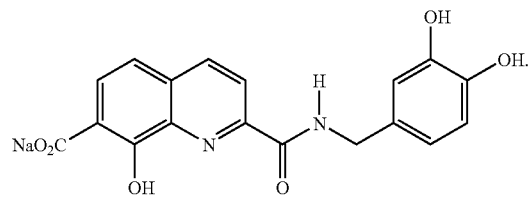

* * * * *